(12) United States Patent
Basu et al.

(10) Patent No.: US 8,388,948 B2
(45) Date of Patent: Mar. 5, 2013

(54) CYTOCOMPATIBLE ALGINATE GELS

(75) Inventors: Shubhayu Basu, Mountain View, CA (US); Gene Michal, San Francisco, CA (US); Florian Ludwig, Lucerne (CH); Jinping Wan, Sunnyvale, CA (US); John Stankus, Campbell, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/525,158

(22) Filed: Jun. 15, 2012

(65) Prior Publication Data
US 2012/0251508 A1 Oct. 4, 2012

Related U.S. Application Data

(62) Division of application No. 11/857,878, filed on Sep. 19, 2007, now Pat. No. 8,221,744.

(51) Int. Cl.
*A01N 63/00* (2006.01)
*C12N 5/071* (2010.01)

(52) U.S. Cl. .................... 424/93.7; 435/366
(58) Field of Classification Search ............ 424/93.7; 435/395
See application file for complete search history.

(56) References Cited

U.S. PATENT DOCUMENTS

| | | | |
|---|---|---|---|
| 4,659,655 A | 4/1987 | Rose | |
| 2002/0081729 A1 | 6/2002 | Peters et al. | |
| 2006/0233850 A1 | 10/2006 | Michal | |
| 2006/0253068 A1 | 11/2006 | Van Bilsen et al. | |
| 2007/0218118 A1 | 9/2007 | Michal et al. | |
| 2007/0249044 A1* | 10/2007 | Desai et al. | 435/325 |
| 2009/0035855 A1* | 2/2009 | Ying et al. | 435/377 |

FOREIGN PATENT DOCUMENTS

| | | |
|---|---|---|
| WO | WO 00/61668 | 10/2000 |
| WO | WO 2006/113828 | 10/2006 |
| WO | WO 2007/048831 | 5/2007 |

OTHER PUBLICATIONS

Smidsrod, O, "Alginate as immobilization matrix for cells" Trends in Biotechnology, vol. 8 1990, 71-78.*
International Search Report for PCT/US2008/070664, mailed Feb. 11, 2009, 20 pgs.
Invitation to Pay Additional Fees for PCT/US2008/070664, mailed Dec. 3, 2008, 11 pgs.
Blindt et al., "Abciximab Inhitits the Migration and Invasion Potential of Human Coronary Artery Smooth Muscle Cells", J. Mol. Cell Cardiol 32, pp. 2195-2206 (2000).
Coller, "Anti-GPIIb/IIIa Drugs: Strategies and Future Directions", Thromb Haemost 86, pp. 427-443 (2001).
Fittkau et al., "The selective modulation of endothelial cell mobility on RGD peptide containing surfaces by YIGSR peptides", Biomaterials 26, pp. 167-174 (2005).
Gombotz et al. "Protein release from alginate matrices", Adv. Drug Delivery Rev. 31, pp. 267-285 (1998).
Harris et al., "Effect of pegylation on pharmaceuticals", Nature Reviews, Drug Discovery vol. 2, No. 3, pp. 1474-1784 (2003).
Kim et al., "Polymeric worm micelles as nano-carriers for drug delivery", Nanotechnology 16, pp. S484-S491 (2005).
Kong et al. "Designing alginate hydrogels to maintain viability of immobilized cells", Biomaterials, pp. 4023-4029 (2003).
Kouvroukoglou et al., "Endothelial cell migration on surfaces modified with immobilized adhesive peptides", Biomaterials 21, pp. 1725-1733 (2000).
Kuo "Tissue engineering seminar series: ionically crosslinked alginate hydrogels as scaffolds for tissue engineering", XP002512102 pp. 1-7 (2002).
Leor et al., Bioengineered Cardiac Grafts, A New Approach to Repair the Infarcted Myocardium?, Circ. Am. Heart Assoc. vol. 102, No. 19 Suppl., pp. III-56 to III-61 (2000).
Lorenceau et al., "Generation of Polymerosomes from double-Emulsions", Langmuir 21, pp. 9183-9186 (2005).
Mann et al., "Cell adhesion peptides alter smooth muscle cell adhesion, proliferation, migration, and matrix protein synthesis on modified surfaces and in polymer scaffolds", John Wiley & Sons, Inc, pp. 86-93 (2002).
Pautot et al, "Production of Unilamellar Vesicles Using an Inverted Emulsion", Langmuir 19, pp. 2870-2879 (2003).
Sajid et al., "$\alpha_v \beta_3$—Integrin antagonists inhibit thrombin-induced proliferation and focal adhesion formation in smooth muscle cells", Am. J. Physiol. Cell Physiol 285, pp. C1330-C1338 (2003).
Seifert et al., "Porous alginate-poly(ethylene glycol) entrapment system for the cultivation of mammalian cells", Biotechnology progress vol. 13, No. 5, pp. 569-576 (1997).
Srivatsa et al., "Selective $\alpha$ v $\beta$ 3 integrin blockade potently limits neointimal hyperplasia and lumen stenosis following deep coronary arterial stent injury: Evidence for the functional importance of integrin $\alpha$ v $\beta$ 3 and osteopontin expression during neointima formation", Cardiovascular Res. 36 pp. 408-428 (1997).
Wheatley et al., "Particles as Drug Delivery Systems", Particulate Sci. and Tech. vol. 5, pp. 53-65 (1987).
Whitaker et al., "The production of protein-loaded microparticles by supercritical fluid enhanced mixing and spraying", J. of controlled release vol. 101, No. 1-3, pp. 85-92 (2005).
Wong, "Alginates in Tissue Engineerin", Methods in Molecular Biology vol. 238, pp. 77-86 (2004).

* cited by examiner

*Primary Examiner* — Jon P Weber
*Assistant Examiner* — Charles Zoltan Constantine
(74) *Attorney, Agent, or Firm* — Squire Sanders (US) LLP; Randy Shen, Esq.

(57) ABSTRACT

The present invention relates to a method of making cytocompatible alginate gels and their use in the treatment of cardiomyopathy.

5 Claims, No Drawings

CYTOCOMPATIBLE ALGINATE GELS

RELATED APPLICATIONS

This application is a divisional of U.S. application Ser. No. 11/857,878, filed on Sep. 19, 2007 and entitled "CYTOCOMPATIBLE ALGINATE GELS," which is hereby incorporated by reference herein in its entirety.

FIELD OF THE INVENTION

This invention relates to the fields of organic chemistry, polymer science, material science and medical science. In particular, it relates to a method of making a cytocompatible alginate gel composition for cellular treatment of cardiovascular diseases, in particular cardiomyopathy.

BACKGROUND OF THE INVENTION

Ischemic heart disease typically results from an imbalance between the myocardial blood flow and the metabolic demand of the myocardium. Progressive atherosclerosis with increasing occlusion of coronary arteries leads to a reduction in coronary blood flow. Atherosclerosis is a type of arteriosclerosis in which cells including smooth muscle cells and macrophages, fatty substances, cholesterol, cellular waste product, calcium and fibrin build up in the inner lining of a body vessel. Arteriosclerosis is thickening and hardening of arteries. Blood flow can be further decreased by additional events such as changes in circulation that lead to hypoperfusion, vasospasm or thrombosis.

Myocardial infarction (MI) is one form of heart disease that often results from the sudden lack of supply of oxygen and other nutrients. The lack of blood supply is a result of a closure of the coronary artery (or any other artery feeding the heart) which nourishes a particular part of the heart muscle. The cause of this event is generally attributed to arteriosclerosis in coronary vessels.

Formerly, it was believed that an MI was caused by a slow progression of closure from, for example, 95% then to 100%. However, an MI can also be a result of initially minor blockages where, for example, there is a rupture of a cholesterol plaque, subsequent formation of blood clots in the artery resulting in blockage of the flow of blood and eventual downstream cellular damage. This damage can cause irregular rhythms that can be fatal, even though the remaining muscle is strong enough to pump a sufficient amount of blood. As a result of this insult to the heart tissue, scar tissue tends to naturally form.

Various procedures, including mechanical and medicinal, are known for reopening blocked arteries. An example of a mechanical procedure is balloon angioplasty with stenting, while an example of a medicinal treatment is the administration of a thrombolytic agent, such as urokinase. Such procedures do not, however, treat actual tissue damage to the heart. Other systemic drugs, such as ACE-inhibitors and beta-blockers, may be effective in reducing cardiac load post-MI, although a significant portion of the population that experiences a major MI ultimately develop heart failure.

An important component in the progression to heart failure is post-MI remodeling of the heart due to mismatched mechanical forces between the infarct region and the healthy tissue resulting in uneven stress distribution in the wall of the left ventricle. The principle components of remodeling include myocyte death, edema and inflammation, followed by fibroblast infiltration and collagen deposition, and finally scar formation. The main component of the scar is collagen. Since mature myocytes of an adult are not regenerated, the infarct region experiences significant thinning. Myocyte loss is the major etiologic factor of wall thinning and chamber dilation that may ultimately lead to cardiomyopathy. Further, remote regions of the heart may experience hypertrophy (thickening) resulting in an overall enlargement of the left ventricle. These changes in the heart often result in changes in a patient's lifestyle, e.g., the ability to walk and to exercise. These changes also correlate with physiological changes that result in increase in blood pressure and worsening systolic and diastolic performance.

Another means of treating post-MI complications such as cardiomyopathy is dynamic cardiomyoplasty wherein a patient's latissimus dorsi muscle is wrapped around the ventricles and electostimulated in synchrony with the contractions of the heart by means of an implanted cardio-myostimulator. A relatively recent modification of dynamic cardiomyoplasty is cellular cardiomyoplasty in which individual cells are delivered to the damaged myocardium where they integrate into the myocardial tissue proliferate and eventually provide an improvement in contractile force. The cells may be, without limitation, fetal or embryonic cardiomyocytes, adult cardiomyocytes, skeletal myoblasts, smooth muscle cells, bone marrow derived stromal cells, undifferentiated blood cells and the like. The problem is delivering the cells to the damaged myocardium and retaining them there in a fully operative condition until the cells have had the opportunity to achieve their therapeutic effect either by secretion of a plethora of cytokinies, or by integrating into the heart tissue and or/by trans-differentiating into cardiomyocytes.

What is needed, then, is a method of delivering cells to the damaged myocardium and retaining the cells at the myocardial locus in their native fully potent state until they have had the opportunity to exert their therapeutic benefit. The current invention provides such a method and a composition to use with the method.

SUMMARY OF THE INVENTION

Thus, in one aspect, the current invention relates to a method of forming a cytocompatible alginate gel, comprising:

providing an alginate;

dispersing substantially homogeneously within the alginate a plurality of cells;

dispersing substantially homogeneously within the alginate a plurality of vesicles; and adding to the alginate a divalent metal cation to form an alginate gel.

In an aspect of this invention, the plurality of cells are selected from the group consisting of localized cardiac progenitor cells, mesenchymal stem cells, bone marrow derived mononuclear cells, adipose tissue derived stem cells, embryonic stem cells, umbilical cord blood derived stem cells, smooth muscle cells and skeletal myoblasts.

In an aspect of this invention, the plurality of vesicles are selected from the group consisting of liposomes and polymerosomes and other multilamellar vesicles.

In an aspect of this invention, the divalent metal cation comprises $Ca^{++}$.

In an aspect of this invention, the vesicles comprise one or more substances that are released from the vesicles and that thereupon enhance the cytocompatibility of the alginate gel that is formed.

In an aspect of this invention, the one or more substances comprise growth factors.

In an aspect of this invention, the growth factors are selected from the group consisting of isoforms of vasoendothelial growth factor (VEGF), fibroblast growth factor (FGF, e.g. beta-FGF), Del 1, hypoxia inducing factor (HIF 1-alpha), monocyte chemoattractant protein (MCP-1), nicotine, platelet derived growth factor (PDGF), insulin-like growth factor 1 (IGF-1), transforming growth factor (TGF alpha), hepatocyte growth factor (HGF), estrogens, Follistatin, Proliferin, Prostaglandin E1 and E2, tumor necrosis factor (TNF-alpha), Interleukin 8 (Il-8), hematopoietic growth factors, erythropoietin, granulocyte-colony stimulating factors (G-CSF) and platelet-derived endothelial growth factor (PD-ECGF).

In an aspect of this invention, the one or more substances comprise cell adhesion proteins.

In an aspect of this invention, the cell adhesion proteins are selected from the group consisting of laminin, fibronectin, RGD, synthetic RGD and cyclic RGD (c-RGD).

In an aspect of this invention, a composition comprising an alginate gel prepared by the above method.

An aspect of this invention is a method of forming a cytocompatible alginate gel, comprising:
providing an alginate;
dispersing substantially homogeneously within the alginate a plurality of cells;
dispersing substantially homogeneously within the alginate a micronized tissue construct; and
adding to the alginate a divalent metal cation to form an alginate gel.

In an aspect of this invention, the plurality of cells are selected from the group consisting of localized cardiac progenitor cells, mesenchymal stem cells, bone marrow derived mononuclear cells, adipose tissue derived stem cells, embryonic stem cells, umbilical cord blood derived stem cells, smooth muscle cells and skeletal myoblasts.

In an aspect of this invention, the micronized tissue construct are selected from the group consisting of urinary bladder matrix (UBM) and small intestinal sub-mucosa (SIS).

In an aspect of this invention, the divalent metal cation comprises $Ca^{++}$.

In an aspect of this invention, a composition comprising a cytocompatible alginate gel prepared by the above method.

An aspect of this invention is a method of forming a cytocompatible alginate gel, comprising:
providing an alginate;
dispersing substantially homogeneously within the alginate a plurality of cells;
dispersing substantially homogeneously within the alginate a plurality of nano or microparticles, wherein:
the microparticles comprise an alginate lyase; and
a divalent metal cation to form an alginate gel.

In an aspect of this invention, the plurality of cells are selected from the group consisting of localized cardiac progenitor cells, mesenchymal stem cells, bone marrow derived mononuclear cells, adipose tissue derived stem cells, embryonic stem cells, umbilical cord blood derived stem cells, smooth muscle cells and skeletal myoblasts.

In an aspect of this invention, the divalent metal cation comprises $Ca^{++}$.

In an aspect of this invention, the nano or microparticles comprise alginate lyases.

In an aspect of this invention, a composition comprising an alginate gel prepared by the above method.

An aspect of this invention is a method of forming a cytocompatible alginate gel, comprising:
providing an alginate;
dispersing substantially homogeneously within the alginate a plurality of cells;
dispersing substantially homogeneously within the alginate an alginate lyase; and
adding to the alginate a divalent metal cation to form an alginate gel.

In an aspect of this invention, the plurality of cells are selected from the group consisting of localized cardiac progenitor cells, mesenchymal stem cells, bone marrow derived mononuclear cells, adipose tissue derived stem cells, embryonic stem cells, umbilical cord blood derived stem cells, smooth muscle cells and skeletal myoblasts.

In an aspect of this invention, the divalent metal cation comprises $Ca^{++}$.

In an aspect of this invention, a composition comprising an alginate gel prepared by the above method.

An aspect of this invention is a method of forming a cytocompatible alginate gel, comprising:
providing an alginate;
dispersing substantially homogeneously within the alginate a plurality of cells;
dispersing substantially homogeneously within the alginate a PEGylated alginate lyase within a degradable microsphere; and
adding to the alginate a divalent metal cation to form an alginate gel.

In an aspect of this invention, the plurality of cells are selected from the group consisting of localized cardiac progenitor cells, mesenchymal stem cells, bone marrow derived mononuclear cells, adipose tissue derived stem cells, embryonic stem cells, umbilical cord blood derived stem cells, smooth muscle cells and skeletal myoblasts.

In an aspect of this invention, the divalent metal cation comprises $Ca^{++}$.

In an aspect of this invention, a composition comprising an alginate gel prepared by the above method.

An aspect of this invention is a method of forming a cytocompatible alginate gel, comprising:
providing an alginate;
subjecting to a treatment that lowers the molecular weight of the alginate;
dispersing substantially homogeneously within the alginate a plurality of cells; and
adding to the alginate a divalent metal cation to form an alginate gel.

In an aspect of this invention, the plurality of cells are selected from the group consisting of localized cardiac progenitor cells, mesenchymal stem cells, bone marrow derived mononuclear cells, adipose tissue derived stem cells, embryonic stem cells, umbilical cord blood derived stem cells, smooth muscle cells and skeletal myoblasts.

In an aspect of this invention, the divalent metal cation comprises $Ca^{++}$. In an aspect of this invention, a composition comprising an alginate gel prepared by the above method.

An aspect of this invention is a method of forming a cytocompatible alginate gel, comprising:
providing an alginate;
subjecting the alginate to oxidation;
dispersing substantially homogeneously within the alginate a plurality of cells; and
adding to the alginate a divalent metal cation to form an alginate gel.

In an aspect of this invention, the plurality of cells are selected from the group consisting of localized cardiac progenitor cells, mesenchymal stem cells, bone marrow derived mononuclear cells, adipose tissue derived stem cells, embryonic stem cells, umbilical cord blood derived stem cells, smooth muscle cells and skeletal myoblasts.

In an aspect of this invention, the divalent metal cation comprises Ca$^{++}$.

In an aspect of this invention, a composition comprising an alginate gel prepared by the above method.

An aspect of this invention is a method of treating a disease in a patient in need thereof, comprising deploying a cytocompatible alginate gel at or near a site where the disease is occurring or is suspected may occur.

In an aspect of this invention, the disease is myocardial infarction (MI).

In an aspect of this invention, the disease is myocardial ischemia.

In an aspect of this invention, the disease is myocarditis.

In an aspect of this invention, the disease is cardiomyopathy.

DETAILED DESCRIPTION OF THE INVENTION

Use of the singular herein includes the plural and visa versa unless expressly stated to be otherwise. That is, "a" and "the" refer to one or more of whatever the word modifies. For example, "a liposome" or "a polymerosome" includes one such particle, two such particles or a large plurality of such particles. Likewise, "a divalent metal cation" or "the divalent cation" may refer to one, two or plethora of such cations, and so on.

As used herein, "substantial" or "substantially" refers to a condition that when so modified is understood to not necessarily be absolute or perfect but would be considered close enough to those of ordinary skill in the art to warrant designating the condition as being present. As a non-limiting example, if cells or vesicles are characterized as being "substantially homogenously" dispersed in a medium, 80% or more homogeneous dispersion would be understood by one of ordinary skill in the art to fulfill the requirement.

As used herein, "homogeneous" or "homogeneously" refers to a solution or layer in which a solute or dispersant is uniformly dispersed throughout a dispersing medium such that a sample taken from anywhere in the solution or the layer will have the same composition as a sample taken from anywhere else in the solution or layer.

As used herein, "dispersing" refers to distribution of one material such as, without limitation, cells, vesicles or particles in a chosen medium.

As used herein, a "gel" or "hydrogel" refers to a water-insoluble substance that nevertheless is capable of imbibing a substantial amount of water, the substance swelling in the process. Thus, the "alginate gel" of the present invention comprises alginate that has been ionically cross-linked to render the alginate water insoluble. The alginate nevertheless retains an affinity for water and absorbs substantial quantities of it while not actually dissolving in the water.

As used herein, "alginate" refers to a linear polysaccharide derived from seaweed. The most common source of alginate is the species Macrocystis pyrifera. Alginate is composed of repeating units of D-mannuronic (M) and L-guluronic acid (G), presented in both alternating blocks and alternating individual residues. Soluble alginate may be in the form of monovalent salts including, without limitation, sodium alginate, potassium alginate and ammonium alginate.

As used herein, a "vesicle" refers to a microscopic particle having a hollow core enclosed within a shell-like structure. The shell may be unilamellar or multilamellar, that is, it may consist of one layer or multiple layers such as the layers of an onion. The hollow core may be filled only with air or it may be filled with a liquid. Examples of vesicles useful in this invention include liposomes, polymerosomes and any other unilamellar or multilamellar particle that exhibits the requisite characteristics described below.

As used herein, a "liposome" refers to a vesicle consisting of an aqueous core enclosed by one or more phospholipid layers. Liposomes may be unilamellar, composed of a single bilayer, or they may be multilamellar, composed of two or more concentric bilayers. Liposomes range from about 20-100 nm diameter for small unilamellar vesicles (SUVs), about 100-5000 nm for large multilamellar vesicles and ultimately to about 100 microns for giant multilamellar vesicles (GMVs). LMVs form spontaneously upon hydration with agitation of dry lipid films/cakes which are generally formed by dissolving a lipid in an organic solvent, coating a vessel wall with the solution and evaporating the solvent. Energy is then applied to convert the LMVs to SUVs, LUVs, etc. The energy can be in the form of, without limitation, sonication, high pressure, elevated temperatures and extrusion to provide smaller single and multi-lamellar vesicles. During this process some of the aqueous medium is entrapped in the vesicle. Generally, however, the fraction of total solute and therefore the amount of therapeutic agent entrapped tends to be rather low, typically in the range of a few percent. Recently, liposome preparation by emulsion templating (Pautot, et al., *Langmuir*, 2003, 19:2870) has been described. Emulsion templating comprises, in brief, the preparation of a water-in-oil emulsion stabilized by a lipid, layering of the emulsion onto an aqueous phase, centrifugation of the water/oil droplets into the water phase and removal of the oil phase to give a dispersion of unilamellar liposomes. This method can be used to make asymmetric liposomes in which the inner and outer monolayers of the single bilayer contain different lipids. Liposomes prepared by any method, not merely those described above, may be used in the compositions and methods of this invention. Any of the preceding techniques as well as any others known in the art or as may become known in the future may be used as compositions of therapeutic agents in or on a delivery interface of this invention. Liposomes comprising phospho- and/or sphingolipids may be used to deliver hydrophilic (water-soluble) or precipitated therapeutic compounds encapsulated within the inner liposomal volume and/or to deliver hydrophobic therapeutic agents dispersed within the hydrophobic bilayer membrane.

Polymerosomes can be prepared in the same manner as liposomes. That is, a film of a diblock copolymer can be formed by dissolving the copolymer in an organic solvent, applying a film of the copolymer-containing solvent to a vessel surface, removing the solvent to leave a film of the copolymer and then hydrating the film. This procedure, however, tends to result is a polydispersion of micelles, worm micelles and vesicles of varying sizes. Polymerosomes can also be prepared by dissolving the diblock copolymer in a solvent and then adding a poor solvent for one of the blocks, which will result in the spontaneous formation of polymerosomes.

As with liposomes, polymerosomes can be used to encapsulate therapeutic agents by including the therapeutic agent in the water used to rehydrate the copolymer film. Polymerosomes can also be force-loaded by osmotically driving the therapeutic agent into the core of the vesicle. Also as with liposomes, the loading efficiency is generally low. Recently, however, a technique has been reported that provides polymerosomes of relative monodispersivity and high loading efficiency; generation of polymerisomes from double emulsions. Lorenceau, et al., *Langmuir*, 2005, 21:9183-86. The technique involves the use of microfluidic technology to generate double emulsions consisting of water droplets surrounded by a layer of organic solvent. These droplet-in-a- drop structures are then dispersed in a continuous water phase. The diblock copolymer is dissolved in the organic solvent and self-assembles into proto-polymerosomes on the concentric interfaces of the double emulsion. The actual polymerosomes are formed by completely evaporating the organic solvent from the shell. Using this procedure the size of the polymerosomes can be finely controlled and, in addition, the ability to maintain complete separation of the internal fluids from the external fluid throughout the process allows extremely efficient encapsulation. This technique along with any other technique known in the art or as may become known in the future can be used to prepare a composition of therapeutic agents for use in or on a delivery interface of this invention.

As used herein, a "divalent metal cation" refers to a positively charged ion of any metallic element of the Periodic Table having a valence of two. Representative examples of divalent metal cations include, but are not limited to, $Ca^{+2}$, $Sr^{+2}$, $Ba^{+2}$, $Mg^{+2}$, $Fe^{+2}$, $Mn^{+2}$, $Cu^{+2}$, $Pb^{+2}$, $Ni^{+2}$, $Co^{+2}$ and $Zn^{+2}$.

As used herein, "cytocompatible" or "cytocompatibility" refers to the ability of a carrier substance, herein an alginate gel, to co-exist for a substantial period of time with a variety of cells dispersed within the substance without the substance having any deleterious effect on the cells, that is, without limitation, any negative effect on their robustness, viability, morphology, physiology, their ability to grow, their ability to proliferate, their ability to express whatever cytokines they normally express in their natural environment and the like. For the purposes of the current invention a substantial period of time constitutes at least 14 days.

Heart diseases include, but are not limited to, myocardial infarction, myocardial ischemia, myocarditis, or cardiomyopathy.

As used herein, "myocardial infarction (MI)" refers to the death of or damage to part of the heart muscle due to an insufficient blood supply.

As used herein, "myocardial ischemia" refers to deficient blood flow to part of the heart muscle.

As used herein, "myocarditis" refers to the inflammation of the heart muscle (myocardium)

As used herein, "cardiomyopathy" refers to a disease of heart muscles in which the heart muscles become inflamed.

Endogenous cardiomyocyte (myocytes) apoptosis is the major etiological factor of wall thinning and chamber dilation and may ultimately lead to progression of cardiomyopathy. After an infarction, mature myocytes of an adult are not regenerated which can lead to significant thinning in the infarct region. Thus, factors which promote survival of cells applied to the infarct region should be beneficial. In some embodiments, cell survival promoting factors include growth factors such as insulin-like growth factor (IGF-1) and human growth factor (HGF), which are known to mediate cell growth, differentiation and survival of a variety of cell types. In addition, small molecules such as HMG-CoA reductase inhibitors (statins) and capsase inhibitors can also promote cell survival and inhibit apoptosis.

To assist in the generation of new cells at the infarct region, autologous or allogeneic stem cells may be delivered to a patient. As used herein, "autologous" refers to the donor and recipient of the stem cells being the same, i.e., the patient him/herself is the source of the cells. As used herein, "allogeneic" refers to the donor and recipient of the stem cells being different individuals. Cell survival promoting factors can be used to increase the survivability of autologous and allogeneic implanted stem cells at the infarct region.

Cardiac progenitor cells are highly specialized stem cells which have shown the ability to differentiate into certain types of fully mature cardiac tissue. Examples of cardiac progenitor cells include, but are not limited to, c-Kit(+), Sca-1(+) and Isl-1(+). Factors which recruit endogenous factors when applied to the infarct region should also be beneficial. In some embodiments, the endogenous recruiting factor can include hepatocyte growth factor (HGF). HGF has been shown to control cell motility and promote cell migration. If applied post-infarction, HGF can assist in mobilizing and recruiting resident cardiac progenitor cells to the infarct region. In some embodiments, the endogenous recruiting factor can include stromal cell-derived factor 1 (SDF-1). SDF-1 is the ligand for the CXCR4 receptor, which is a surface receptor on circulating endothelial progenitor cells. When applied in or around the infarct region, SDF-1 may facilitate the homing of circulating endothelial progenitor cells to induce neovascularization.

While alginate gels increase cell retention at the target site when co-injected with cells in vitro and in vivo, the cells are viable for only around 14 days. The cytocompatibility of alginate gels is limited because of very small pore size (40-200 nm) which does not allow spreading of the cells which are usually in the range of 5-40 microns in size depending upon the cell type. However, the pore size is still large enough to allow nutrient transfer to the cells, hence the observed period of viability.

A relatively high concentration of calcium ions (at least 40 mM) is required to effect the gelation of alginate (at 0.5% w/v solution). Excess calcium, however, is detrimental to cells and can potentially cause arrhythmias when injected into the myocardium. The alginate gels are cross-linked with the calcium ions, which cross-links cannot be degraded by cellular enzymes to allow cell migration. A larger pore size, one that would permit migration and proliferation of the cells, should prove extremely beneficial.

In an embodiment of this invention, cells and vesicles are homogeneously dispersed in an alginate followed by addition of a divalent metal cation. A presently preferred divalent metal cation is $Ca^{++}$. The vesicles of the present invention include, but are not limited to, liposomes, polymerosomes or other multilamellar vesicles. The vesicles are transformed from a spherical structure to a cochlear structure in the presence of $Ca^{++}$. When the calcium chloride is added to the alginate dispersion, the calcium ions first crosslink the alginate. Excess calcium ions are then quenched by the liposomes, polymerosomes or other multilamellar vesicles to form cochlear structures. The result is more open pore space in the alginate gel as the large spatial volumes occupied by the vesicles prior to contact with $Ca^{++}$ remain after the vesicles collapse into condensed cochlear structures. Thus, the larger pores in the alginate gels are conducive to cell migration and cell proliferation. In addition, the quenching of the calcium ions by the vesicles is beneficial to prevent arrhythmias.

In another embodiment, the vesicles comprise one or more substances that are released from the vesicles. These substances include, but not limited to, growth factors. The growth factors are selected from the group consisting of isoforms of vasoendothelial growth factor (VEGF), fibroblast growth factor (FGF, e.g. beta-FGF), Del 1, hypoxia inducing factor (HIF 1-alpha), monocyte chemoattractant protein (MCP-1), nicotine, platelet derived growth factor (PDGF), insulin-like growth factor 1 (IGF-1), transforming growth factor (TGF alpha), hepatocyte growth factor (HGF), estrogens, Follistatin, Proliferin, Prostaglandin E1 and E2, tumor necrosis factor (TNF-alpha), Interleukin 8 (Il-8), hematopoietic growth factors, erythropoietin, granulocyte-colony stimulating factors (G-CSF) and platelet-derived endothelial growth factor (PD-ECGF). The growth factors which are released from the vesicles further enhance the cytocompatibility of the alginate gel that is formed.

In a further embodiment, the vesicles comprise cell adhesion proteins. The cell adhesion proteins are selected from the group consisting of laminin, fibronectin, RGD, synthetic RGD and cyclic RGD (c-RGD). The polypeptide Arg-Gly-Asp (RGD) has been demonstrated to be a bioactive factor for human endothelial cell attachment and therefore would be expected to assist in the attachment of cells of this invention as well. In addition to RGD itself, cyclic RGD (cRGD) and RGD mimetics and small molecules capable of binding as does RGD to other adhesion receptors differentially expressed on the endothelial cells are within the scope of this invention. Some examples of cRGD or RGD mimetics include V3 antagonists such as llb/llb antagonists (B. S. Coller, *Thromb. Haemost.* 2001, 86:427-443 (Review)), such as abciximax (R. Blindt, *J. Mol. Cell. Cardiol.* 2000, 32:2195-2206), XJ 735 (S. S. Srivastva et al., *Cardiovasc. Res.* 1997, 36:408-428), anti-$_3$-integrin antibody F11, cRGD (M. Sajid et al., *Am. J. Physiol. Cell Physiol.*, 2003, 285:C1330-1338), and other sequences such as laminin derived SIKVAV (M. H. Fittkau et al., *Biomaterials*, 2005, 26:167-174), laminin derived YIGSR (S. Kouvroukoglou et al., *Biomaterials,* 2000, 21:1725-1733), KQAGDV, and VAPG (B. K. Mann, *J. Biomed. Mater. Res.* 2002, 60:86-93).

In yet another embodiment, an alginate is homogeneously dispersed with cells and micronized tissue construct followed by addition of the divalent metal cation. The micronized tissue constructs are selected from the group consisting of urinary bladder matrix (UBM) and small intestinal sub-mucosa (SIS). The UBM or SIS is ground and sieved to achieve a sub 100 micron particle size. This micronized tissue is added to an alginate solution (Pronova LVG or LVM, 0.2 to 1.0% solids in PBS, preferably 0.5%), at a level of 0.1 to 3% by weight of total solution. The micronized tissue are dispersed throughout the alginate and the cells. The cells secrete proteases to degrade the urinary bladder matrix (UBM) and small intestinal sub-mucosa (SIS). The voids left by the degraded UBM or SIS can provide speading room for the cells.

In an embodiment, an alginate is homogeneously dispersed with cells and nano or microparticles comprising an enzyme and the divalent metal cation. The one or more enzymes are selected from the group consisting of alginate lyases. The alginate lyases cause the breakdown of the alginate as it is being cross-linked resulting in larger open spaces in the gel when it forms. These larger spaces are compatible with cell growth and proliferation and thus the procedure should enhance the cytocompatibility of the alginate gel with the cells.

As used herein, "PEG" refers to polyethylene glycol (PEG).

As used herein, "PEGylation" or "PEGylated" refers to a process of attaching the PEG to other molecules. To couple PEG to a molecule, the PEG is first activated by preparing a derivative of the PEG that results in the PEG having a good leaving group at one end. The molecule to be PEGylated must have an active functional group capable of displacing the leaving group.

In one embodiment, an alginate is homogeneously dispersed with cells, followed by addition of the divalent metal cation and a suspension of degradable microspheres (e.g. PLGA) containing PEGylated alginate lyase. The PEGylation of an alginate lyase lengthens its circulation time and inhibits its degradation by proteases.

In another embodiment, an alginate is subjected to a treatment that lowers the molecular weight of the alginate, and then homogeneously dispersed with a plurality of cells followed by the addition of the divalent metal cation, when a cytocompatible alginate gel is formed. The various treatments which reduce molecular weight of an alginate include, but are not limited to, gamma irradiation, e-beaming, UV irradiation or combinations thereof. The alginate may be treated dry or in solution. The reduction in the molecular weight of the alginate by these means would have the same beneficial effect in terms of creating larger voids in the alginate gel as the above discussed lyase addition.

In further embodiment, an alginate is subjected to an oxidation that partially oxidizes the alginate, and then homogeneously dispersed with cells, followed by addition of the divalent metal cation, when a cytocompatible alginate gel is formed. The oxidation would result in a more hydrolytically labile polymer chain and should result again in the formation of larger voids or pores in the alginate gel with resultant increase in cytocompatibility of the alginate gel that is formed.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed:

1. A method of forming a cytocompatible alginate gel, comprising:
   providing an alginate;
   dispersing substantially homogeneously within the alginate a plurality of cells;
   dispersing substantially homogeneously within the alginate particles of a micronized tissue construct, wherein the particles are less than 100 microns in size and constitute less than 10% by weight of the alginate; and
   adding to the alginate a divalent metal cation to form an alginate gel.

2. The method of claim 1, wherein the plurality of cells are selected from the group consisting of localized cardiac progenitor cells, mesenchymal stem cells, bone marrow derived mononuclear cells, adipose tissue derived stem cells, embryonic stem cells, umbilical cord blood derived stem cells, smooth muscle cells and skeletal myoblasts.

3. The method of claim 1, wherein the micronized tissue construct are selected from the group consisting of urinary bladder matrix (UBM) and small intestinal sub-mucosa (SIS).

4. The method of claim 1, wherein the divalent metal cation comprises Ca++.

5. A composition comprising an alginate gel prepared by the method of claim 1.

* * * * *